US009724289B2

(12) United States Patent
Bernet et al.

(10) Patent No.: US 9,724,289 B2
(45) Date of Patent: Aug. 8, 2017

(54) GRANULATED DRY CLEANSER FOR THE CARE OF KERATINOUS SUBSTRATES

(75) Inventors: Claire-Sophie Bernet, Nivelles (BE); Serge Creutz, Liege (BE); Stephanie Postiaux, Ressaix (BE); Flore Martine Jeanne Vandemeulebroucke, Manage (BE)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 13/390,130

(22) PCT Filed: Aug. 3, 2010

(86) PCT No.: PCT/US2010/044182
§ 371 (c)(1),
(2), (4) Date: Feb. 13, 2012

(87) PCT Pub. No.: WO2011/019539
PCT Pub. Date: Feb. 17, 2011

(65) Prior Publication Data
US 2012/0171264 A1 Jul. 5, 2012

Related U.S. Application Data

(60) Provisional application No. 61/233,572, filed on Aug. 13, 2009.

(51) Int. Cl.
*A61K 8/891* (2006.01)
*A61Q 17/04* (2006.01)
*A61Q 15/00* (2006.01)
*A61K 8/97* (2017.01)
*B05D 1/02* (2006.01)
*A61Q 5/12* (2006.01)
*A61Q 5/02* (2006.01)
*A61K 8/92* (2006.01)
*A61Q 5/06* (2006.01)
*A61K 8/02* (2006.01)
*A61K 8/898* (2006.01)
*A61K 8/895* (2006.01)
*A61K 8/25* (2006.01)
*A61K 8/26* (2006.01)
*A61K 8/73* (2006.01)

(52) U.S. Cl.
CPC ............ *A61K 8/895* (2013.01); *A61K 8/0225* (2013.01); *A61K 8/0279* (2013.01); *A61K 8/25* (2013.01); *A61K 8/26* (2013.01); *A61K 8/732* (2013.01); *A61K 8/898* (2013.01); *A61Q 5/02* (2013.01); *A61K 2800/31* (2013.01); *A61K 2800/412* (2013.01); *A61K 2800/624* (2013.01); *A61K 2800/654* (2013.01)

(58) Field of Classification Search
None
See application file for complete search history.

(56) References Cited

U.S. PATENT DOCUMENTS

| 4,035,267 A * | 7/1977 | Gleckler et al. ............... 132/202 |
| 4,450,151 A * | 5/1984 | Shinozawa ..................... 424/46 |
| 4,451,387 A | 5/1984 | Tai |
| 5,641,480 A * | 6/1997 | Vermeer ................. A61K 8/046 424/70.1 |
| 6,004,584 A * | 12/1999 | Peterson et al. .............. 424/489 |
| 6,497,862 B2 * | 12/2002 | Oku ......................... A61K 8/60 424/401 |
| 2002/0094341 A1* | 7/2002 | Jorgensen et al. ............ 424/401 |
| 2003/0219391 A1 | 11/2003 | Liew et al. |
| 2004/0265347 A1 | 12/2004 | Auguste et al. |
| 2005/0152932 A1* | 7/2005 | Normand ................. A61K 8/11 424/401 |
| 2007/0275021 A1* | 11/2007 | Lee et al. ..................... 424/401 |

FOREIGN PATENT DOCUMENTS

| JP | H08239311 A | 9/1996 |
| JP | 2003267850 A | 9/2003 |
| JP | 2003277216 | 10/2003 |
| JP | 2005097246 A | 4/2005 |
| JP | 2008163133 A | 7/2008 |
| WO | 03049711 | 6/2003 |
| WO | WO-03049711 | * 6/2003 |
| WO | 2007031801 | 3/2007 |
| WO | WO-2007-031801 | * 3/2007 |
| WO | 2009153311 | 12/2009 |

OTHER PUBLICATIONS

English abstarct of WO2003049711, Jun. 2003.*
Certified English translation of WO2003049711, Jun. 2003.*
Pyle, "What's the difference between Shredding, Grinding, and Granulating?", Aug. 18, 2010, retrieved from http://www.jordanreductionsolutions.com/blog/the-difference-between-shredding-grinding-and-granulating/.*
Mintel; Jan. 8, 2009, High coverage pressed powder UV.
Chinese Office Action (Translated and original), Apr. 21, 2014, 15 pages.
She Zhenbao et al, Processing and Use of Zeolite, Chemical Industry Publishing House, Jul. 2005, pp. 43 to 45, 219.
Zheng Shuilin, "Surface Modification of Powders", Building Materials Industry Publishing House, Aug. 2003, pp. 1 to 2, 19, 68 to 69, 77, 91 to 93, 126.
English language abstract and machine translation for JPH08239311 (A) extracted from http://worldwide.espacenet.com database on Feb. 8, 2017, 20 pages.
English language abstract and machine translation for JP2008163133 (A) extracted from http://worldwide.espacenet.com database on Feb. 7, 2017, 19 pages.
Handbook of Pharmaceutical Granulation Technology, Second Edition, Dilip M. Parikh, Synthon Pharmaeuticals Inc., Research Triangle Park, North Carolina, USA, 2005 by Taylor & Francis Group, LLC, 624 pages.

* cited by examiner

Primary Examiner — Jianfeng Song
(74) Attorney, Agent, or Firm — Warner Norcross & Judd LLP

(57) ABSTRACT

Described herein is a granulated dry composition comprising at least one non-elastomeric polyorganosiloxane, agglomerated onto solid carrier particles. The granulated dry compositions can be used as a dry cleanser for keratinous substrates with high speed of absorption of body fluids together with improved sensory feel and release of care agents.

9 Claims, No Drawings

GRANULATED DRY CLEANSER FOR THE CARE OF KERATINOUS SUBSTRATES

RELATED APPLICATIONS

This application claims priority to and all the advantages of International Patent Application No. PCT/US2010/044182, filed on Aug. 3, 2010, which claims priority to U.S. Provisional Patent Application No. 61/233,572, filed on Aug. 13, 2009.

BACKGROUND OF THE INVENTION

Disclosed herein is a granulated powder to be used as a dry cleanser for keratinous substrates with high speed of absorption of body fluids together with improved sensory feel and release of care agents. By dry is generally meant that water is not needed during application. In the present description, we use the term "cleanser" to include cleaning personal care product which is designed to clean skin or hair for animals as well as for human beings. A dry cleanser is designed to remove body fluids, such as sebum, perspiration and malodor, dirt, skin particles, dandruff, environmental pollutants or other contaminant particles that gradually build up on keratinous substrates. The personal care product may be functional with respect to the portion of the body to which it is applied; it can be cosmetic, therapeutic, or some combination thereof, through the release of care agents such as sensory agent, shine agent, coloring agent, fragrance, moisturizing agent or refreshing agent. The cleanser as described herein is in the form of a powder able to clean hair or skin in the absence of water.

Cleansers are usually sold in liquid format and require the use of water and the drying of the keratinous substrate afterwards. There is however a requirement for dry application, i.e. in the absence of water, particularly if water is not available or not allowed, e.g. travels, hospital or during working hours, or if there are some transportation restriction, e.g. in airports. To sufficiently absorb sebum, a dry cleanser needs to be left long enough on the keratinous substrate, thus limiting their use. There is therefore the need to enhance the speed of absorption and thus reduce the needed contact time with the keratinous substrate.

It has been found that the agglomeration of non-elastomeric polyorganosiloxanes with solid particulate carriers enhances the speed of absorption of body fluids by these carriers, though these non-elastomeric polyorganosiloxanes have no specific absorption properties.

BRIEF SUMMARY OF THE INVENTION

Described herein is a granulated dry composition comprising at least one non-elastomeric polyorganosiloxane, agglomerated onto solid carrier particles. By granules we mean agglomerated particles, typically free flowing particles, as opposed to slurry agglomerate. The granules comprise carrier particles upon which a liquid non-elastomeric polyorganosiloxane containing composition is deposited in combination with optional care agents and which exhibit fast absorbency.

The granulated dry composition is prepared by contacting a liquid non-elastomeric polyorganosiloxanes containing composition (liquid composition), with a solid particulate carrier composition (carrier) under conditions such that the liquid composition is agglomerated with the carrier, the agglomerated product being kept in granule form during agglomeration or subsequently formed into granules.

We have found that the granulated dry composition absorbs body fluids faster and is perceived as providing a pleasant feel on the hair or skin. The granulated dry composition may be packaged in various types of packaging or dispenser, such as but not limited to sachet, flask, aerosol.

DETAILED DESCRIPTION OF THE INVENTION

The solid particulate carriers which may be used in the invention include zeolites, for example Zeolite 4A or Zeolite X, and other aluminosilicates or silicates, for example magnesium silicate, calcium silicate, sodium silicate, mica, bentonite, diatomite, sepiolite, natural or modified clays, such as that sold under the Trade Mark 'Laponite XG', talc, neat or treated silica, cellulose, alginates, chitin, chitosan, starch, for example granulated starch or native starch, calcium sulphate, calcium carbonate, sodium sulphate, sodium acetate, magnesium sulphate, phosphates, for example powdered or granular sodium tripolyphosphate, sodium bicarbonate, sodium perborate, sodium citrate, wood flour and carbohydrates such as cellulose derivatives, for example sodium carboxymethylcellulose, or sugars, for example lactose, dextrose, or maltodextrin, for example that sold under the Trade Mark 'Glucidex IT'. Soft carriers are preferred to hard carriers, so that the granulated cleanser composition feels soft to the touch. Typically the solid particulate carrier is one that is able to absorb body fluids such as sebum. The carrier may comprise a mixture of different carriers, for example calcium silicate and starch for improved absorbency.

The mean particle size of a soft solid particulate carrier which contacts the liquid composition is generally from 1 micrometer to 250 micrometers, alternatively from 1 to 100 micrometers, alternatively from 2 up to 15 or 30 micrometers.

The mean particle size of a hard solid particulate carrier is 1 to 30 micrometers, alternatively 1 to 20 micrometers, alternatively 1 to 10 micrometers.

The liquid composition comprises at least one non-elastomeric polyorganosiloxane, optionally a binder and optionally a cosmetic ingredient.

The non-elastomeric polyorganosiloxanes which may be used herein may be in the form of oils, waxes, resins or gums, possibly modified with organic moieties, and may be soluble or non soluble in the liquid composition. They may be volatile or non-volatile. Any combination or mixture of different non-elastomeric polyorganosiloxanes may also be used. Such non-elastomeric polyorganosiloxanes are known to the person skilled in the art as are methods for making them and many of them commercially available. Elastomeric polyorganosiloxane do not form part of the polyorganosiloxanes which may be used herein.

Volatile non-elastomeric polyorganosiloxanes are typically those having a boiling point below 250° C., such as (i) cyclic polyorganosiloxanes containing from 3 to 7 alternatively from 5 to 6 silicon atoms; (ii) linear volatile polyorganosiloxanes having 2 to 9 silicon atoms and having a viscosity of less than or equal to 5 mm$^2$/s at 25° C. The volatile non-elastomeric polyorganosiloxanes may also be mixtures of (i) and (ii). The volatile non-elastomeric polyorganosiloxanes may be further exemplified by volatile methyl siloxane or volatile ethyl siloxanes.

Non-volatile non-elastomeric polyorganosiloxanes may be exemplified by polyalkylsiloxanes, polyarylsiloxanes, polyalkylarylsiloxanes, polyorganosiloxane gums and resins, polyorganosiloxanes modified with organofunctional groups, and mixtures thereof.

Examples of polyalkylsiloxanes, are polydimethylsiloxanes containing trimethylsilyl end groups (CTFA designation Dimethicone) having a viscosity of from 5 mm$^2$/s to 2.5 million mm$^2$/s at 25° C., alternatively 10 to 1 million mm$^2$/s. Also suitable are polydimethylsiloxanes containing dimethylsilanol end groups (CTFA designation Dimethiconol).

Polyalkylarylsiloxanes which are useful may be chosen from linear and branched polydimethylmethylphenylsiloxanes and polydimethyldiphenylsiloxanes with a viscosity of from 10 to 50 000 mm$^2$/s at 25° C.

The non-elastomeric polyorganosiloxane may be in the form of a gum. Gums are typically polydiorganosiloxanes having a molecular weight in the range of 200,000 and 1,000,000, used alone or in conjunction with a solvent. This solvent may be chosen from volatile polyorganosiloxanes, polydimethylsiloxane (PDMS) oils, isoparaffins, hydrocarbon solvents, or mixtures thereof.

The non-elastomeric polyorganosiloxane may be a resin. Non-elastomeric polyorganosilxoane resins which may be used herein typically consist of siloxane units of the general formula R"SiO$_{3/2}$ wherein R" denotes a hydrocarbon-based group having from 1 to 16 carbon atoms or a phenyl group; alternatively a $C_1$-$C_4$ lower alkyl radical; alternatively methyl, or a phenyl radical. The non-elastomeric polyorganosiloxane resins usefule herein may be used alone or in conjunction with a solvent. The resins may be exemplified by an organopolysiloxane resin (CTFA designation Trimethylsiloxysilicate) or those described in U.S. Pat. Nos. 5,152,984 and 5,126,126, such as Aminopropyl Phenyl Trimethicone (CTFA designation).

Non-elastomeric polyorganosiloxanes modified with an organofunctional group (organomodified polyorganosiloxane) may be used herein. By modified with an organofunctional group it is meant polyorganosiloxanes containing in their structure one or more organofunctional groups attached via a Si—C or Si—O—C linkage.

One type of organomodified polyorganosiloxane is polyorganosiloxanes containing polyethylenoxy and/or polypropylenoxy groups, optionally containing $C_6$-$C_{24}$ alkyl groups and substituted or unsubstituted amine groups such as $C_1$-$C_4$ aminoalkyl groups (aminofunctional polyorganosiloxanes).

One example of aminofunctional polyorganosiloxanes are those having the formula $R^2R_2SiO(R_2SiO)_a(R^1RSiO)_b SiR_2R^2$ or $R^2R_2SiO(R_2SiO)_a(R^1SiO_{3/2})_bSiR_2R^2$ wherein R is a monovalent hydrocarbon radical, $R^1$ is an aminoalkyl group having its formula selected from the group consisting of —$R^3NH_2$ and —$R^3NHR^4NH_2$ wherein $R^3$ is a divalent hydrocarbon radical having at least 3 carbon atoms and $R^4$ is a divalent hydrocarbon radical having at least 2 carbon atoms, $R^2$ is selected from the group consisting of R, $R^1$, and —OH, typically —OH; subscript a has a value of 0 to 2000, alternatively 50 to 2000, and subscript b has a value of from greater than zero to 200, alternatively 1 to 100.

In these aminofunctional polyorganosiloxanes, the R radicals are exemplified by alkyl radicals such as the methyl, ethyl, propyl, butyl, amyl, and hexyl, alkenyl radicals such as the vinyl, allyl, and hexenyl, cycloalkyl radicals such as the cyclobutyl and cyclohexyl, aryl radicals such as the phenyl and naphthyl, aralkyl radicals such as the benzyl and 2-phenylethyl, alkaryl radicals such as the tolyl, and xylyl, halohydrocarbon radicals such as 3-chloropropyl, 4-bromobutyl, 3,3,3-trifluoropropyl, chlorocyclohexyl, bromophenyl, and chlorophenyl. Typcially R is a monovalent hydrocarbon radical having from 1 to 6 carbon atoms, alternatively methyl, phenyl, and vinyl.

In the above aminofunctional polyorganosiloxane, $R^3$ is typically an alkylene radical having from 3 to 20 carbon atoms such as propylene, —$CH_2CHCH_3$—, butylene, —$CH_2CH(CH_3)CH_2$—, pentamethylene, hexamethylene, 3-ethyl-hexamethylene, octamethylene, or decamethylene.

In the above aminofunctional polyorganosiloxane, $R^4$ is typically an alkylene radical having from 2 to 20 carbon atoms such as ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

Specific examples of $R^1$ are $CH_2CH_2CH_2NHCH_2CH_2NH_2$ and —$CH_2CH(CH_3)CH_2NHCH_2CH_2NH_2$ or their salts. Examples of such salts include alkyl carboxylate salts, aryl carboxylate salts, halide salts such as chlorides and bromides, and other neutralization products of the amines with organic acids.

The aminofunctional polyorganosiloxanes typically have from 0.1 to 15 mol % of the above described amino groups alternatively from 0.2 to 10 mol %. The aminofunctional polyorganosiloxanes useful in this invention may be prepared by procedures well known in the art. Many of these polyorganosiloxanes are available commercially.

Other suitable aminofunctional polyorganosiloxanes include those having alkoxylated groups; or hydroxyl groups, as described in EP 1081272, U.S. Pat. Nos. 6,171,515 and 6,136,215 such as Bis-Hydroxy/Methoxy Amodimethicone.

Other aminofunction polyorganosiloxanes which may be used herein are amino-acid functional siloxanes obtained by reacting an amino acid derivative selected from the group of an N-acyl amino acid and an N-aroyl amino acid with an amino functional siloxane, further described in WO 2007/141565.

Other aminofunctional polyorganosiloxanes which may be used herein are quaternary ammonium functional polyorganosiloxanes, described in U.S. Pat. Nos. 6,482,969 and 6,607,717, such as Polyorganosiloxane Quaternium-16 (CTFA designation).

Other aminofunction polyorganosiloxanes which may be used herein are amino ABn polyorganosiloxane polyether block copolymer, where an amino functionality is added to the ABn polyorganosiloxane polyether copolymer, also described in IP.COM 00141525 such as Bis-Isobutyl PEG/PPG-20/35/Amodimethicone Copolymer (CTFA designation).

Other organomodified polyorganosiloxanes which may be used herein are water soluble or water dispersible polyorganosiloxane polyether compositions. These are also known as polyalkylene oxide polyorganosiloxane copolymers, polyorganosiloxane poly(oxyalkylene) copolymers, polyorganosiloxane glycol copolymers, or polyorganosiloxane surfactants. These may be linear rake or graft type materials, or ABA and ABn types where the B is the siloxane polymer block, and the A is the poly(oxyalkylene) group. The poly (oxyalkylene) group may consist of polyethylene oxide, polypropylene oxide, or mixed polyethylene oxide/polypropylene oxide groups. Other oxides, such as butylene oxide or phenylene oxide are also possible.

Other organomodified polyorganosiloxanes which may be used herein are hydrocarbyl functional organopolysiloxanes comprising a siloxy unit of the formula $R^5R'_iSiO_{(3-i)/2}$ wherein R' is any monovalent hydrocarbon group, but typically is an alkyl, cycloalkyl, alkenyl, alkaryl, aralkyl, or aryl group containing 1-20 carbon atoms, $R^5$ is a hydrocarbyl group having the formula —R$^6$OCH$_2$CH$_2$OH, wherein R$^6$ is a divalent hydrocarbon group containing 2 to 6 carbon atoms and i has a value of from zero to 2. Such hydrocarbyl functional organopolysiloxanes are further described in U.S. Pat. Nos. 2,823,218, 5,486,566, 6,060,044 and US20020524. The hydrocarbyl functional organopolysiloxanes may be exemplified by those designated by CTFA as Bis-Hydroxyethoxypropyl Dimethicone.

Yet another organomodified polyorganosiloxane which may be used herein may be siloxane-based polyamide. U.S. Pat. No. 6,051,216 discloses siloxane-based polyamides as gelling agents for cosmetic products, methods for making such agents, and formulations thereof. Such polyamides contain siloxane groups in the main chain and act to thicken compositions containing volatile and/or non-volatile polyorganosiloxane fluids. Variants of siloxane-based polyamides such as polyorganosiloxane polyether-amide block copolymers described in US 2008/004568,may also be used herein.

Yet more organomodified polyorganosiloxanes which may be used herein may be vinyl-type polymer having a carbosiloxane dendrimer structure on their side molecular chain. These may be used as neat polymer or as a solution or a dispersion in a liquid such as a polyorganosiloxane oil, organic oil, alcohol, or water. Such polymers which may be used herein are further described in EP 0963751,and are given the CTFA designation Acrylates/Polytrimethylsiloxymethacrylate Copolymer.

Other organomodified polyorganosiloxanes which may be used herein may be alkylmethylsiloxane materials which may be present as liquids or waxes. In liquid form they can be either cyclic having a structure [MeR$^7$SiO]$_p$[Me$_2$SiO]$_q$ or linear having a structure R8Me$_2$SiO(MeR$^7$SiO)$_w$(Me$_2$SiO)$_x$ SiR Me$_2$ wherein each R$^7$ is independently a hydrocarbon of 6 to 30 carbon atoms, R$^8$ is methyl or R$^7$, p is 1-6,q is 0-5,w is 0-5 and x is 0-5,provided p+q is 3-6 and q is not 0 if R$^8$ is methyl. These liquids may be either volatile or non-volatile and they can have a wide range of viscosities such as from 0.65 to 50,000 mm$^2$/s at 25° C.

Alkylmethylsiloxane waxes have the structure R$^8$Me$_2$SiO (Me$_2$SiO)$_y$(MeR$^7$SiO)$_z$SiMe$_2$R$^8$ wherein y is 0-100,z is 1-100,R$^7$ is an alkyl group of 6-30 carbon atoms and R$^8$ is methyl or R$^7$. Typically the alkylmethylsiloxane has the formula Me$_3$SiO(Me$_2$SiO)$_y$(Me R$^7$SiO)$_z$SiMe$_3$. These alkylmethylsiloxane materials are known in the art and can be produced by known methods.

Other organomodified polyorganosiloxanes which may be used herein may be polyorganosiloxane quaternary ammonium compounds or monoquaternary ammonium functional derivatives of alkanolamino polydimethylsiloxanes, such as disclosed in U.S. Pat. No. 5,026,489. The derivatives are exemplified by (R$^9$$_3$SiO)$_2$Si R$^9$(CHR$^{10}$)$_c$NR$^{10}$$_d$R$^{11}$$_{3-d}$ wherein R$^9$ is an alkyl group, R$^{10}$ is H, alkyl, or aryl, R$^{11}$ is (CHR$^{10}$)OH, c is 1 to 10,and d is 1 to 3.

Other organomodified polyorganosiloxanes which may be used herein may be saccharide-siloxane copolymer having a saccharide component and an organosiloxane component and linked by a linking group, such as described in WO 2006/127883,EP 1885331 and US 2008/0199417. The saccharide-siloxane copolymer has the following formula: R$^{12}$$_e$R$^{13}$$_{(3-e)}$SiO[(SiR$^{12}$R$^{13}$O)$_m$(SiR$^{12}$O)$_n$]$_v$SiR$^{13}$$_{(3-e)}$R$^{12}$$_e$ wherein each R$^{13}$ may be the same or different and comprises hydrogen, C$_1$-C$_{12}$ alkyl, an organic radical, or R$^3$—W, W comprises an epoxy, cycloepoxy, primary or secondary amino, ethylenediamine, carboxy, halogen, vinyl, allyl, anhydride, or mercapto functionality, m and n are integers from 0 to 10,000 and may be the same or different, each e is independently 0, 1, 2, or 3, v is an integer such that the copolymer has a molecular weight less than 1 million, R$^{12}$ has the formula —Z(G$^1$)$_f$(G$^2$)$_g$, and there is at least one R$^{12}$ per copolymer, wherein G$^1$ is a saccharide component comprising 5 to 12 carbons, f+g is 1 to10,f or g can be 0,G$^2$ is a saccharide component comprising 5 to 12 carbons additionally substituted with organic or organosilicon radicals, Z is the linking group and is independently selected from the group consisting of: R$^{15}$NHC(O)R$^{16}$—; R$^{15}$NHC(O) OR$^{16}$—; R$^{15}$NH—C(O)NHR$^{16}$—; R$^{15}$C(O)OR$^{16}$—; R$^{15}$OR$^{16}$—; R$^{15}$CH(OH)CH$_2$OR$^{16}$—; R$^{15}$SR$^{16}$—; R$^{15}$CH (OH)CH$_2$NHR$^{16}$; and R$^{15}$N(R$^1$)R$^{16}$—, where R$^{15}$ and R$^{16}$ are divalent spacer groups comprising (R$^{17}$)$_r$(R$^{18}$)$_s$(R$^{19}$)$_t$, where at least one of r, s and t must be 1,and R$^{17}$ and R$^{19}$ are either C$_1$-C$_{12}$ alkyl or ((C$_1$-C$_{12}$)O)$_k$ where k is any integer 1-50 and each (C$_1$-C$_{12}$)O may be the same or different, R$^{18}$ is —N(R$^{20}$)—, where R$^{20}$ is H or C$_1$-C$_{12}$ alkyl, or is Z—X where Z is previously defined or R$^{15}$. X is a carboxylic acid, phosphate, sulfate, sulfonate or quaternary ammonium radical, and at least one of R$^{15}$ and R$^{16}$ must be present in the linking group and may be the same or different, and wherein the saccharide-siloxane copolymer is a reaction product of a functionalized organosiloxane polymer and at least one hydroxy-functional saccharide such that the organosiloxane component is covalently linked via the linking group, Z, to the saccharide component.

The saccharide-siloxane copolymer which may be used herein may be ionically-modified saccharide siloxane copolymers, such as described in WO 2006/127924.

Organofunctional polyorganosiloxanes having at least one substituent that is a sulfonate group are useful herein. The sulfonate groups typically has the formula —R$^{21}$G(CO) PhSO$_3$Y$^+$ where R$^{21}$ is a divalent organic group bonded to the organopolysiloxane; Y is hydrogen, an alkali metal, or a quaternary ammonium; G is an oxygen atom, NH, or an NR$^{22}$ group where R$^{22}$ is a monovalent organic group such as those having 1 to 20 carbon atoms, alternatively 1 to 10 carbon atoms, and Ph is a phenyl cycle. The sulfonate group substituent is bonded to the organopolysiloxane via a Si—C bond by the R$^{21}$ moiety.

R$^{21}$ is typically a divalent hydrocarbon group containing 2 to 6 carbon atoms such as ethylene, propylene, butylene, pentylene, or hexylene group. Alternatively, R$^{21}$ is a propylene group, —CH$_2$CH$_2$CH$_2$— or an isobutylene group, —CH$_2$CH(CH$_3$)CH$_2$—.

G in the general formula for the sulfonate substituent group above is an oxygen atom, NH, or an NR$^{22}$ group where R$^{22}$ is a monovalent organic group. Typically, G is NH. R$^{22}$ may be exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; amine functional organic groups such as aminopropyl and aminoethylaminoisobutyl; a polyalkylene oxide (polyether) such as polyoxyethylene, polyoxypropylene, polyoxybutylene, or mixtures thereof, and halogenated hydrocarbon groups such as 3,3,3-trifluoropropyl, 3-chloropropyl, and dichlorophenyl.

The non-elastomeric polyorganosiloxanes useful herein include non-volatile polyorganosiloxanes chosen from the family of polyalkylsiloxanes containing trimethylsilyl end groups, polyalkylsiloxanes containing dimethylsilanol end groups, such as dimethiconol, polysiloxanes containing amine groups, such as amodimethicones or trimethylsilylamodimethicones, polysiloxanes containing polyethylenoxy and/or polypropylenoxy groups, hydrocarbyl functional organopolysiloxane and mixtures of two or more of these. Also useful are emulsions of any of these and in situ polymerized emulsions.

The polyorganosiloxane is typically liquefied before adding to the solid particulate composition. For example, the polyorganosiloxanes may be in the form of a fluid or an emulsion or a suspension when it is mixed with the solid particulate composition. Where an emulsion or suspension is used, the water present in the emulsion or suspension forms some or all of the water required to solubilize the other ingredients present in the liquid composition. Suitable polydiorganosiloxane emulsions are described for example in EP 432951,EP 798332,EP 0874017,U.S. Pat. No. 6,013,682,EP 1263840 and EP 1054032.

A binder may also be added to improve the stability of the granules. Examples of binders are polycarboxylates, for example polyacrylic acid or a partial sodium salt thereof or a copolymer of acrylic acid, for example a copolymer with maleic anhydride, polyoxyalkylene polymers such as polyethylene glycol, which may be applied molten or as an aqueous solution, reaction products of tallow alcohol and ethylene oxide, or cellulose ethers, particularly water-soluble or water-swellable cellulose ethers such as sodium carboxymethylcellulose, or sugar syrup binders such as Polysorb 70/12/12 or LYCASIN 80/55 HDS maltitol syrup or Roclys C1967 S maltodextrin solution.

Polycarboxylate binders are water soluble polymers, copolymers or salts thereof. They have at least 60% by weight of segments with the general formula:

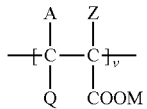

wherein A, Q and Z are each selected from the group consisting of hydrogen, methyl, carboxy, carboxymethyl, hydroxy and hydroxymethyl, M is hydrogen, alkali metal, ammonium or substituted ammonium and v is from 30 to 400. Typically A is hydrogen or hydroxy, Q is hydrogen or carboxy and Z is hydrogen. Suitable polymeric polycarboxylates include polymerised products of unsaturated monomeric acids, e.g. acrylic acid, maleic acid, maleic anhydride, fumaric acid, itaconic acid, aconitic acid, mesaconic acid, citraconic acid and methylenemalonic acid. The copolymerisation with lesser amounts of monomeric materials comprising no carboxylic acid, e.g. vinylmethyl, vinylmethylethers, styrene and ethylene is not detrimental to the use of the polycarboxylates of the present invention. Depending on the type of polycarboxylate this level can be kept low, or levels can be up to 40% by weight of the total polymer or copolymer.

The polycarboxylates binders are polyacrylates having an average viscosity at 25° C. in mPa·s from 50 to 10,000, alternatively 2,000 to 8,000 and a molecular weight of 1,000 to 500,000,alternatively 3,000 to 100,000,alternatively 15,000 to 80,000. Examples of polycarboxylate binders are acrylate/maleate or acrylate/fumarate copolymers or their sodium salts having a ratio of acrylate to maleate or fumarate segments from 30:1 to 2:1.

The binder may be mixed with the liquid composition before being deposited on the carrier, or alternatively is deposited on the carrier particles either at the same time or subsequently to the liquid carrier, or at both times. In any case, the binder should be liquid, being solubilised or molten. The binder may be used at 0.1 to 10% by weight of the granulated dry composition.

The granulated dry compositions may contain other ingredients or additive substances such as perfumes, fragrances, colorants such as dyes, essential oils, deposition agents such as polyquaternary compounds to improve the deposition of additive substances from the dry cleanser onto hair or skin, buffering agents, stabilizers, proteins, preservatives, antidandruff agent, disinfectants, glycols, polyols such as glycerine and propylene glycol, vitamins and/or their derivatives, styling agents, sunscreen agents, humectants, oil components, emollients, esters, ceramides, soothing ingredients, antiperspirants, malodor sequestrants, surfactants, amino-acid derivatives, antioxidants, botanicals, antimicrobial agents and silicone elastomers. Such ingredients may be mixed into the liquid composition before granulation or mixed with the solid particulate carrier composition before granulation or they can be mixed to the granulated dry composition.

Antidandruff agents useful herein include compounds such as pyridinethione salts, selenium compounds such as selenium disulfide, and soluble antidandruff agents.

Hair dyeing agents useful herein include oxidation hair dyeing agents, no-oxidation dyeing agents and semi-permanent dyeing agents. Oxidation dye agents penetrate into hair, and chemically impart a colour to the hair by means of colour formation resulting from oxidative polymerisation under the action of an oxidation agent. Non-oxidation dyeing agents are used for semi-permanent or non-permanent hair dyeing. Semi-permanent or non-oxidation dyeing agents are sometimes also referred to as direct dyes. Semi-permanent dyeing will usually colour human hair for up to six subsequent shampoo washes, although a high proportion of colour is often lost after 2 or 3 washes. Semi-permanent hair dyeing compositions are usually provided as single-component products, and may contain a variety of additives in addition to a direct dye.

Conditioners useful herein are typically in the form of organic cationic conditioning agents for the purpose of providing more hair grooming. Such cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7,Polyquaternium-8,Polyquaternium-10,Polyquaternium-11,and Polyquaternium-23. The above cationic organic polymers and others are described in more details in U.S. Pat. No. 4,240,450 which is hereby incorporated by reference to further describe the cationic organic polymers. Other categories of conditioners such as cationic surfactants such as cetyl trimethylammonium chloride, cetyl trimethylammonium bromide, and stearyltrimethylammonium chloride, may also be employed in the compositions as a cationic conditioning agent.

A cationic deposition aid may also be used. The cationic deposition aid may be a polymer or be formed from two or more types of monomers. The molecular weight of the polymer will generally be 5,000 and 10,000,000,typically at least 10,000 alternatively 100,000 to 2,000,000. The polymers will have cationic nitrogen containing groups such as quaternary ammonium or protonated amino groups, or a mixture thereof. The cationic charge density has been found to need to be at least 0.1 meq/g, alternatively above 0.8 or higher. The cationic charge density should not exceed 4 meq/g, alternatively it is less than 3, alternatively less than 2 meq/g. The charge density may be measured using the Kjeldahl method and should be within the above limits at the desired pH of use, which will in general be from 3 to 9 and alternatively from 4 to 8. The cationic nitrogen-containing group will generally be present as a substituent on a fraction of the total monomer units of the cationic deposition polymer. Thus when the deposition aid is not a polymer it may contain spacer noncationic monomer units. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethydiallyammonium chloride, referred to in the industry (CTFA) as Polyquaternium-6 and Polyquaternium-7,respectively; mineral acid salts of aminoalkyl esters of homo-and co-polymers of unsaturated carboxylic acids having from 3 to 5 carbon atoms, as described in U.S. Pat. No. 4,009,256; and cationic polyacrylamides as described in WO 95/22311. Other cationic deposition aids that may be used include polysaccharide polymers, such as cationic cellulose derivatives and cationic starch derivatives. Cationic polysaccharide polymer materials suitable for use in compositions of the invention include those of the formula: $A-O(R-N^+R^1R^2R^3X^-)$ wherein: A is an anhydroglucose residual group, such as starch or cellulose anhydroglucose residual, R is an alkylene oxyalkylene, polyoxyalkylene, or hydroxyalkylene group, or combination thereof, R1,R2 and R3 independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in R1,R2 and R3) alternatively being 20 or less, and X is an anionic counterion , as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418,incorporated herein by reference), and copolymers of etherified cellulose and starch (e.g., as described in U.S. Pat. No. 3,958,581, incorporated herein by reference). The cationic deposition aid may be put in the liquid composition or added in solid form to the particulate carrier composition.

The granulated dry composition may contain proteins, like those extracted from wheat, soy, rice, corn, keratin, elastin or silk. Most are in the hydrolyzed form and they may also be quaternised to provide better performance.

Another additive that may be included in the granulated dry composition is a perfume or fragrance. The perfume may be a fragrant odoriferous substance or a mixture of fragrant odoriferous substances including natural substances obtained by extraction of flowers, herbs, leaves, roots, barks, wood, blossoms or plants; artificial substances including mixtures of different natural oils or oil constituents; and synthetically produced substances. Some examples of perfume ingredients that are useful include hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; and undecalactone gamma.

Additional examples of perfume ingredients include orange oil; lemon oil; grapefruit oil; bergamot oil; clove oil; dodecalactone gamma; methyl-2-(2-pentyl-3-oxo-cyclopentyl) acetate; beta-naphthol methylether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiff's base of 4-(4-hydroxy-4-methylpentyl)-3-cyclohexene-1-carboxaldehyde and methyl anthranilate; cyclic ethyleneglycol diester of tridecandioic acid; 3,7-dimethyl-2,6-octadiene-1-nitrile; ionone gamma methyl; ionone alpha; ionone beta; petitgrain; methyl cedrylone; 7-acetyl-1,2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; ambroxane; dodecahydro-3a,6,6,9a-tetramethylnaphtho-2,1bfuran; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy-4- methyl pentyl)-3-cyclohexene-1-carboxaldehyde, and methyl anthranilate.

More examples of perfume ingredients are geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; and ethylene brassylate.

Pediculicides, for control of lice infestations may be present in the granulated dry composition. Suitable pediculicides are well known in the art and include, for example, pyrethrins such as those described in U.S. Pat. No. 4,668,666.

A pH adjusting agent may be used to adjust pH of the granulated dry composition, within the range of 4 to 9 alternatively within the range of 5 to 7. Any water soluble acid such as a carboxylic acid or a mineral acid is suitable. Suitable acids include mineral acids such as hydrochloric acid, sulphuric acid, and phosphoric acid, monocarboxylic acid such as acetic acid and lactic acid, and polycarboxylic acids such as succinic acid, adipic acid, and citric acid.

Typical pigments are iron oxides and titanium dioxide which may be present in either the dry granulated composition in the amount of 0.1 to 30 wt. %, alternatively 0.5 to 20 wt. % alternatively 0.8 to 10 wt. %.

It may be desirable to add various preservatives such as the parabens, BHT, BHA, etc or any usual preservative.

Sunscreen materials include those materials which absorb ultraviolet light from 290-320 nanometers (the UV-B region) such as, para-aminobenzoic acid derivatives and cinnamates such as octyl methoxycinnamate and those which absorb ultraviolet light in the range of 320-400 nanometers (the UV-A region) such as benzophenones and butyl methoxy dibenzoylmethane. Some additional examples of sunscreen materials which may be used herein are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate Vitamins are a class of organic compounds that must be ingested part of the diet for humans (and other organisms) in order to maintain health and well being. Some vitamins also have beneficial effects when applied topically and for this reason are popular ingredients in various personal care formulations, where it is desired that the vitamin should be released after the formulation has been applied to the skin or hair.

Vitamins comprise a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin $D_2$), cholecalciferol (vitamin $D_3$), phytonadione (vitamin $K_1$), and tocopherol (vitamin E). Water-soluble vitamins that have utility in personal care formulations include ascorbic acid (vitamin C), thiamin (vitamin $B_1$) niacin (nicotinic acid), niacinamide (vitamin $B_3$), riboflavin (vitamin $B_2$), pantothenic acid (vitamin $B_5$), biotin, folic acid, pyridoxine (vitamin $B_6$), and cyanocobalamin (vitamin $B_{12}$).

Many of the vitamins that are used in personal care compositions are inherently unstable and therefore present difficulties in the preparation of shelf-stable personal care compositions. The instability of the vitamins is usually related to their susceptibility to oxidation. For this reason, vitamins are often converted into various derivatives that are more stable in personal care formulations. These vitamin derivatives offer other advantages in addition to improved stability. Vitamin derivatives may be more amenable to certain kinds of personal care formulations. For example a lipid-soluble vitamin may be derivatised to produce a water-soluble material that is easier to incorporate into a water-based formulation. Retinol and tocopherol are two lipid-soluble vitamins that are particularly useful in skin care compositions and consequently there are many different derivatives of these two vitamins that are used in personal care compositions. Derivatives of retinol include retinyl palmitate (vitamin A palmitate), retinyl acetate (vitamin A acetate), retinyl linoleate (vitamin A linoleate), and retinyl propionate (vitamin A propionate). Derivatives of tocopherol include tocopheryl acetate (vitamin E acetate), tocopheryl linoleate (vitamin E linoleate), tocopheryl succinate (vitamin E succinate), tocophereth-5,tocophereth-10, tocophereth-12,tocophereth-18,tocophereth-50 (ethoxylated vitamin E derivatives), PPG-2 tocophereth-5,PPG-5 tocophereth-2,PPG-10 tocophereth-30,PPG-20 tocophereth-50,PPG-30 tocophereth-70,PPG-70 tocophereth-100 (propoxylated and ethoxylated vitamin E derivatives), and sodium tocopheryl phosphate. Derivatives of ascorbic acid (Vitamin C) such as ascorbyl palmitate, ascorbyl dipalmitate, ascorbyl glucoside, ascorbyl tetraisopalmitate, and tetrahexadecyl ascorbate may also be used, as may vitamin derivatives incorporating two different vitamins in the same compound, for example ascorbyl tocopheryl maleate, potassium ascorbyl tocopheryl phosphate or tocopheryl nicotinate.

Provitamins may also be used, such as panthenol.

The dry granulated composition may contain one or more water-soluble emollients such as lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

Organic butters, such as mango, cocoa, shea butters, may be used in the dry granulated composition. Typically these butters are added to the liquid composition and may undergo a heating step to be molten either before addition to the liquid composition, or the liquid composition may be heated to allow for the melting of the butters.

Polyorganosiloxane elastomers may also be used herein. The polyorganosiloxane elastomer may be in combination with a polyorganosiloxane oil be dispersed in low polarity organic solvents such as isododecane. The polyorganosiloxane elastomers may have an alkyl, polyether, amine or other organofunctional group grafted onto the polyorganosiloxane elastomer backbone. Suitable polyorganosiloxanes elastomers are taught in U.S. Pat. Nos. 5,811,487, 5,880,210, 6,200,581, 5,236,986, 6,331,604, 6,262,170, 6,531,540 and 6,365,670.

Typical additional ingredients which may be included for specific care of the keratinous substrates include but are not limited to soothing ingredients, for example aloe vera; refreshing ingredients, for example menthyl lactate; and fragrance.

To produce the granulated dry compositions, the liquid composition is contacted with the solid particulate carrier composition in a mixer in which droplets of the liquid composition become agglomerated with carrier particles. Contact may for example be in a granulating mixer, an extruder, a compactor or in a high shear or low shear mixer. Typically the liquid composition is contacted with the solid particulate carrier composition in a granulating mixer in which the agglomerated product is kept in particulate form. The granulating mixer is generally a high shear mixer such as an Eirich™ pan granulator, a Schugi™ mixer, a Paxeson-Kelly™ twin core blender, a Lodige ploughshare mixer, an Aeromatic™ fluidized bed granulator or a Pharma™ drum mixer or a Glatt® fluid bed system. In most granulating mixers, the liquid composition is sprayed onto the solid particulate carrier composition while the solid particulate carrier composition carrier is being agitated or fluidized. The liquid composition may alternatively be poured into the mixer instead of spraying.

The dry granulated composition is generally collected from the mixer and packaged. The product from a vertical continuous granulating mixer may be fed to a fluidised bed which cools and/or dries the granules and fluidises them for transport to a packing station. The distribution of granules at the outlet of the granulating mixer may include fines and oversize material. The fines can for example be recovered in a filter coupled with the fluidized bed cooler and/or in a classification unit and recycled with fresh particles feeding the mixer. Oversize material may be collected, crushed down and mixed with the granulated product in a fluidized bed.

If the liquid composition and the solid particulate carrier composition are combined in an apparatus which does not maintain the mixture as separate granules, for example an extruder or a compactor, the mixture may be converted into granules by flaking, by comminuting an extruded strand or by spheronization after extrusion.

One form of granulating mixer is a vertical continuous granulating mixer comprising blades rotating within a tubular housing and having an inlet for solid particulate carrier composition and a spray inlet for the liquid composition to contact the solid particulate carrier composition above the blades. The blades are mounted on a substantially vertical shaft aligned with the housing and rotating within the housing. The blades have a predetermined clearance from the inner wall of the housing. Contact with the liquid agglomerates the particles into granules; the liquid acts as a binder by absorbing the kinetic energy of colliding particles. The blades maintain the solid particles and granules in motion and prevent agglomeration into granules which are too large. Examples of such vertical continuous granulating mixers are described in U.S. Pat. No. 4,767,217,EP 744215 and WO 03/059520. Vertical continuous granulating mixer technology has the advantage that the residence time in the mixing chamber is very short, for example 1 second, giving the possibility of high throughput.

The ratio of the weight of liquid composition to the weight of solid particulate carrier composition used to produce the granulated dry composition can be varied within wide limits. Generally this ratio is at least 1:99 and may be up to 80:20 or even higher provided that the granules produced are stable and do not agglomerate further under the forces to which they are subjected while being transported. Alternatively, the ratio of the weight of liquid composition fed to the mixer to the weight of solid particulate carrier composition fed to the mixer is in the range 5:95 to 80:20.

Accordingly, the weight ratio of non-elastomeric polyorganosiloxane to solid particulate carrier in the dry granulated composition produced after drying is in the range 2:98 to 80:20,alternatively 4:96 to 40:60 alternatively 15:85 to 75:25. The mean particle diameter of the granules are typically 0.01 to 2 mm, alternatively 0.02 to 1.5 mm. Typically the dry granulated composition comprises at least 80 wt %, alternatively 90 wt %, alternatively 95 wt % of the solid particulate carrier and the non-elastomeric polyorganosiloxane.

In order to ensure adequate coverage of the solid particulate carrier composition with most ingredients of the liquid composition, the solid particulate carrier composition is typically treated in conditions minimizing the risk of volatilization of the components. This may be done by choosing ingredients of low volatility such as non volatile polyorganosiloxanes, or by working at low temperature.

The granulated dry compositions can be used as a dry cleanser for keratinous substrates such as hair or skin. The granulated dry composition may be deposited on hair by sprinkling or spraying or with an applicator, such as a brush or a sponge. It may further be left to stand on hair and absorb sebum and deposit the additive substance (when needed). It is further removed from hair by brushing or air blowing. Hair may then be set as usual.

The granulated dry cleanser composition may be deposited on the skin by sprinkling or spraying or with an applicator, such as a brush or a sponge. It may further be spread and rubbed onto skin to release the care agents. It may be further removed from the skin by air blowing, swiping or any other convenient way.

For easier application on keratinous substrate, the dry granulated composition may be suspended in a propellant and applied through an aerosol. The choice of propellant material is not critical and any nontoxic substance which develops the requisite pressure may be used to perform the essentially mechanical function of driving the volatile liquid and the dry granulated composition out of the aerosol container. All propellants which are commonly used in aerosol cans are suitable for use in this application. Many organic substances or mixtures thereof, may serve as propellant. Liquids with boiling points ranging from −30° to 82° C. may be used as the volatile liquid in conjunction with the granulated dry composition. Compounds with suitable properties include esters, such as ethyl acetate and methyl acetate, ketones, such as methyl ethyl ketone and acetone, hydrocarbons, such as the straight chained alkanes, butanes, pentane and hexane, cyclic hydrocarbons, such as cyclopropane, cyclobutane, cyclopentane, and cyclohexane, branched chain hydrocarbons, such as 2,2-dimethyl propane, methyl pentanes, dimethyl pentanes and dimethyl butanes, alcohols, such as ethyl alcohol and iso-propyl alcohol, ethers, such as dimethyl ether, diethyl ether, diisopropyl ether, methyl ethers of ethyl, isopropyl, propyl, n-butyl, t-butyl and isobutyl alcohols, ethyl ethers of n-propyl, isopropyl, isobutyl, t-butyl and 2-butyl alcohols. Compressed gas may be used, such as nitrogen, carbone dioxide, air.

The application of the granulated dry compositions generally provides conditioning benefits of the keratinous substrate, e.g. skin and hair. Benefits obtained from using the granulated dry compositions on hair according to the invention include typically sebum absorption, hair conditioning, volume, softness, detangling ease, shine/luster, color protection/retention, styling, strengthening, deposition of an additive substance. Benefits obtained from using the granulated dry compositions on skin include body fluids absorption, moisture management, deposition of an additive substance, skin softness, suppleness, moisturization, emolliency.

Furthermore, the powder form provides convenience (ease of transport), new product format and a preservative is not mandatory.

EXAMPLES

The following examples are included to demonstrate embodiments of the invention. It should be appreciated by those of skill in the art that the techniques disclosed in the examples which follow represent techniques discovered by the inventor to function well in the practice of the invention, However, those of skill in the art should, in light of the present disclosure, appreciate that many changes can be made in the specific embodiments which are disclosed and still obtain a like or similar result without departing from the spirit and scope of the invention. All percentages are in wt. % unless otherwise indicated.

Granulation Process Used to Generate Examples

A liquid solution containing polyorganosiloxane and optionally other additives was poured very slowly into a high shear mixer in which the solid particulate carrier is placed. The mixture was stirred continuously until a particulate material is obtained. The particulate material was then passed over an Aeromatic fluid bed for 10 minutes at 50° C. The dry compositions are described in the tables below.

Evaluations Carried Out on Powders

Olive oil was used as "artificial" sebum. Olive oil contains a high amount of triglycerides and fatty acids, which are the main components of natural sebum. To measure the speed of sebum absorption: 0.5 grams of dry granulated composition was spread at the surface of 3 grams of olive oil. The time needed to totally wet the powder was measured. Results are indicated in seconds.

Granulated dry composition sensory feel: panelists were asked to touch the powders with their fingers and rated them vs. a commercially available dry cleanser product (rated at a baseline of 0) or when specified, the solid particulate carrier. A softer sensory feel vs. the reference was reported as "+". On the contrary, if the granulated dry composition was less soft, it was reported as "−".

Comparative Example 1

Commercially available "Gentle Dry Shampoo" product from Laboratoires Klorane was used as a reference. It is composed of oryza sativa rice starch, aluminium starch octenylsuccinate, hectorite, avena sativa oat kernel flour, kaolin, silica, cyclodextrin and fragrance (perfume). Results are given in Table 1.

TABLE 1

| (dry composition) ||
|---|---|
| Absorption time | Sensory feel |
| 220 s | 0 |

Comparative Example 2

Commercial native corn starch was used as received. Results are given in Table 2.

Comparative Example 3

Commercial native corn starch was dry blended with Dimethicone/Vinyldimethicone Crosspolymer, polyorganosiloxane (Dow Corning® 9506 Powder) with an average particle size of 3 μm. Results are given in Table 2.

Example 1

An aqueous non ionic suspension of 60% Dimethicone/Vinyldimethicone Crosspolymer (Dow Corning® 9509 Silicone Elastomer Suspension) was granulated on native corn starch following the granulation process described above.

TABLE 2

| (dry compositions) | | | |
|---|---|---|---|
| Ingredients | Comparative example 2 | Comparative example 3 | Example 1 |
| Corn starch | 100% | 78.9% | 78.9% |
| Dimethicone/Vinyldimethicone Crosspolymer powder | | 21.1% | |
| Dimethicone/Vinyldimethicone Crosspolymer suspension | | | 21.1% |
| Absorption time | 656 s | 400 s | 129 s |
| Sensory feel | − | + | ++ |

Comparative Example 4

Commercial calcium silicate, Calflo E from World Minerals, was used as received. Results are given in Table 3.

Comparative Example 5

Commercial calcium silicate was dry blended with the Dimethicone/Vinyldimethicone Crosspolymer powder of Comparative Example 3. Results are given in Table 3.

Example 2

The aqueous Dimethicone/Vinyldimethicone Crosspolymer suspension of Example 1 was granulated on calcium silicate.

TABLE 3

| (dry compositions) | | | |
|---|---|---|---|
| Ingredients | Comparative example 4 | Comparative example 5 | Example 2 |
| Calcium silicate | 100% | 49.1% | 49.1% |
| Dimethicone/Vinyldimethicone Crosspolymer powder | | 50.9% | |

TABLE 3-continued (dry compositions)

| Ingredients | Comparative example 4 | Comparative example 5 | Example 2 |
|---|---|---|---|
| Dimethicone/Vinyldimethicone Crosspolymer suspension | | | 50.9% |
| Absorption time | 1140 s | 859 s | 635 s |
| Sensory feel | 0 | ++ | + |

Examples 3 and 4

An aqueous non ionic microemulsion of 20% Amodimethicone (3500 mm²/s) (Dow Corning® CE-8170 AF Microemulsion) was granulated on calcium silicate. Results are given in Table 4.

TABLE 4

(dry compositions)

| Ingredients | Comparative example 4 | Example 3 | Example 4 |
|---|---|---|---|
| Calcium silicate | 100% | 63.3% | 57.7% |
| Amodimethicone microemulsion | | 36.7% | 42.3% |
| Absorption time | 1140 s | 476 s | 353 s |
| Sensory feel | 0 | + | ++ |

Comparative Example 6

The Amodimethicone fluid of 3500 mm²/s used in the emulsion of Example 3 was mixed directly with olive oil and was found not miscible, demonstrating the absence of absorbency properties of the Amodimethicone fluid.

Example 5

The aqueous microemulsion of Amodimethicone of Example 3 was granulated on calcium silicate.

Examples 6 and 7

An aqueous non ionic emulsion of 60% Divinyldimethicone/Dimethicone Copolymer (>120,000,000 mm²/s) (Dow Corning® HMW 2220 Non-Ionic Emulsion) was granulated on calcium silicate.

Example 8

Lauryl PEG/PPG-18/18 Methicone (Dow Corning® 5200 Formulation Aid) having a viscosity in the range of 1000-4500 mm²/s, was granulated on calcium silicate.

Example 9

Cetyl Dimethicone (Dow Corning® 2502 Cosmetic Fluid), having a viscosity of 45 mm²/s, was granulated on calcium silicate.

TABLE 5

(dry compositions)

| | Calcium silicate | Polyorganosiloxane | Polyorganosiloxane concentration | Absorption time |
|---|---|---|---|---|
| Comparative example 4 | 100% | | | 1140 s |
| Example 5 | 32.5% | Amodimethicone microemulsion | 67.5% | 97 s |
| Example 6 | 46.1% | Divinyldimethicone/Dimethicone Copolymer emulsion | 53.9% | 414 s |
| Example 7 | 25% | Divinyldimethicone/Dimethicone Copolymer emulsion | 75% | 62 s |
| Example 8 | 23.2% | Lauryl PEG/PPG-18/18 Methicone | 76.8% | 68 s |
| Example 9 | 24.3% | Cetyl Dimethicone | 75.7% | 102 s |

Example 10

The aqueous microemulsion of Amodimethicone used in Example 3 was blended with Vegetol The Vert LC 412 hydro (Propylene Glycol (and) Water (and) Camellia Sinensis Leaf Extract by Gattefossé) and then granulated on calcium silicate.

Example 11

The aqueous microemulsion of Amodimethicone used in Example 3 was blended with Silkerine HL (Sericin by Vama Pharma) and then granulated on calcium silicate.

Example 12

The aqueous microemulsion of Amodimethicone used in Example 3 was blended with *Aloe vera* aqueous extract (Blanova Specialties) and then granulated on calcium silicate.

Example 13

The aqueous microemulsion of Amodimethicone used in Example 3 was blended with Vegetol Aloes GR 198 hydro (Propylene Glycol (and) Water (and) Aloe Ferox Leaf Extract by Gattefossé) and then granulated on calcium silicate.

Example 14

The aqueous microemulsion of Amodimethicone used in Example 3 was blended with Circulatoire 318 HS (Propylene glycol, *Cupressus sempervirens* cone extract, *Hamamelis virginiana* leaf extract, *Ruscus aculeatus* root extract, *Vitis vinifera* leaf extract by Alban Muller) and then granulated on calcium silicate.

Example 15

The aqueous microemulsion of Amodimethicone used in Example 3 was blended with Argane oil and then granulated on calcium silicate.

Example 16

The aqueous microemulsion of Amodimethicone used in Example 3 was blended with Menthyl lactate from Givaudan and then granulated on calcium silicate.

TABLE 6

(dry compositions)

| | Calcium silicate | Amodimethicone microemulsion | Additive | Additive concentration | Absorption time |
|---|---|---|---|---|---|
| Comparative example 4 | 100% | | | | 1140 s |
| Example 10 | 57.2% | 40.6% | Vegetol The Vert LC 412 hydro | 2.2% | 455 s |
| Example 11 | 55% | 40.7% | Silkerine HL | 4.3% | 817 s |
| Example 12 | 56.8% | 41% | Aloe vera aqueous extract | 2.2% | 608 s |
| Example 13 | 56.8% | 41.% | Vegetol Aloes GR 198 hydro | 2.2% | 284 s |
| Example 14 | 56.5% | 41.3% | Circulatoire 318 HS | 2.2% | 637 s |
| Example 15 | 57% | 40.9% | Argane oil | 2.1% | 385 s |
| Example 16 | 56.5% | 41.3% | Menthyl lactate | 2.2% | 1005 s |

Example 17

The aqueous microemulsion of Amodimethicone used in Example 3 was blended with Phenyltrimethicone, having a viscosity of 22.5 mm$^2$/s, known as shine agent, and granulated on calcium silicate.

Example 18

Phenyltrimeticone (Dow Corning® 556 Cosmetic Grade Fluid) was granulated on calcium silicate.

TABLE 7

(dry compositions)

| Ingredients | Comparative example 4 | Example 17 | Example 18 |
|---|---|---|---|
| Calcium silicate | 100% | 56.4% | 23.3% |
| Amodimethicone microemulsion | | 41% | |
| Phenyltrimethicone | | 2.6% | 76.7% |
| Absorption time | 1140 s | 972 s | 73 s |

Example 19

An aqueous emulsion containing 72% of a 50/50 blend of Dimethicone 100 mm$^2$/s and Mango butter (Dow Corning® 7-3123 Mango Blend Emulsion) was granulated on calcium silicate.

Example 20

An aqueous emulsion containing 72% of a 50/50 blend of Dimethicone 100 mm$^2$/s and Shea butter ((Dow Corning® 7-3121 Shea Blend Emulsion) was granulated on calcium silicate.

Example 21

Sunflower oil was granulated on calcium silicate.

Example 22

An aqueous emulsion containing 50% of a 50/50 blend of Amodimethicone (3500 mm$^2$/s) (Dow Corning® 2-8566 Amino Fluid) and sunflower oil was granulated on calcium silicate.

TABLE 8

(dry compositions)

| | Calcium silicate | Polyorganosiloxane/ additive emulsion | Polyorganosiloxane/ additive concentration | Absorption time |
|---|---|---|---|---|
| Comparative example 4 | 100% | | | 1140 s |
| Example 19 | 22.6% | Dimethicone/Mango | 77.4% | 15 s |
| Example 20 | 22.6% | Dimethicone/Shea | 77.4% | 30 s |
| Example 21 | 79.2% | Sunflower oil | 20.8% | 1259 s |
| Example 22 | 35.3% | Amodimethicone/Sunflower oil | 64.7% | 30 s |

Example 23

The aqueous emulsion of the blend Dimethicone/Mango butter as used in Example 19 was granulated on native corn starch.

Example 24

The aqueous emulsion of the blend Dimethicone/Shea butter as used in Example 20 was granulated on native corn starch.

Example 25

The aqueous emulsion of the blend Amodimethicone/Sunflower oil as used in Example 22 was granulated on native corn starch.

TABLE 9

(dry compositions)

| | Corn starch | Polyorganosiloxane/ additive emulsion | Polyorganosiloxane/ additive concentration | Absorption time |
|---|---|---|---|---|
| Comparative example 2 | 100% | | | 656 s |
| Example 23 | 81.3% | Dimethicone/Mango | 18.7% | 57 s |
| Example 24 | 79.1% | Dimethicone/Shea | 20.9% | 78 s |
| Example 25 | 80.3% | Amodimethicone/Sunflower oil | 19.7% | 32 s |

Comparative Example 7

Rice starch was used as received.

Example 26

The aqueous microemulsion of Amodimethicone as used in Example 3 was granulated on rice starch.

Example 27

The aqueous microemulsion of Amodimethicone as used in Example 3 was granulated on native corn starch.

Comparative Example 8

Wood flour was used as received.

Example 28

The aqueous microemulsion of Amodimethicone as used in Example 3 was granulated on wood flour.

Comparative Example 9

Zeolite was used as received.

Example 29

The aqueous microemulsion of Amodimethicone as used in Example 3 was granulated on zeolite.

TABLE 10

(dry compositions)

|  | Carrier | Carrier concentration | Amodimethicone microemulsion | Absorption time |
|---|---|---|---|---|
| Comparative example 7 | Rice starch | 100% |  | 543 s |
| Example 26 | Rice starch | 91.7% | 8.29% | 82 s |
| Comparative example 2 | Corn starch | 100% |  | 656 s |
| Example 27 | Corn starch | 93.7% | 6.32% | 28 s |
| Comparative example 8 | Wood flour | 100% |  | 1000 s |
| Example 28 | Wood flour | 84.9% | 15.07% | 273 s |
| Comparative example 9 | Zeolite | 100% |  | 624 s |
| Example 29 | Zeolite | 92.6% | 7.41% | 120 s |

Example 30

The aqueous microemulsion of Amodimethicone as used in Example 3 was granulated on a mix of calcium silicate and iron oxide pigment (Unipure brown LC881 by LCW Sensient).

TABLE 11

(dry compositions)

|  | Calcium silicate | Pigment | Amodimethicone microemulsion | Absorption time |
|---|---|---|---|---|
| Comparative example 2 | 100% |  |  | 1140 s |
| Example 30 | 55% | 13% | 32% | 510 s |

The invention claimed is:

1. A method of cleansing a keratinous substrate, the method comprising:
    applying a granulated dry composition having granules to the keratinous substrate; and
    removing the granulated dry composition from the keratinous substrate;
    wherein the granules are agglomerated particles having a non-elastomeric polyorganosiloxane in liquid form agglomerated with a solid particulate carrier,
    wherein the solid particulate carrier is capable of absorbing body fluids,
    wherein the mean particle diameter of the granules is 0.02 to 1.5 mm, and
    wherein the weight ratio of the non-elastomeric polyorganosiloxane to the solid particulate carrier is in the range of 2:98 to 80:20, wherein the non-elastomeric polyorganosiloxane is amodimethicone.

2. The method according to claim 1, wherein the granulated dry composition is applied to the keratinous substrate by sprinkling or spraying or with an applicator.

3. The method according to claim 1, wherein the keratinous substrate is hair.

4. The method according to claim 1, wherein the granules further comprise an additive substance and the additive substance is deposited on the keratinous substrate by application of the granulated dry composition.

5. A method of cleansing a keratinous substrate in the absence of water, the method comprising:
    applying a granulated dry composition having granules to the keratinous substrate; and
    removing the granulated dry composition from the keratinous substrate;
    wherein the granules are agglomerated particles having a non-elastomeric polyorganosiloxane in liquid form agglomeratedonte with a solid particulate carrier,
    wherein the solid particulate carrier is capable of absorbing body fluids,
    wherein the mean particle diameter of the granules is 0.02 to 1.5 mm,
    wherein the weight ratio of the non-elastomeric polyorganosiloxane to the solid particulate carrier is in the range of 2:98 to 80:20, and
    wherein the non-elastomeric polyorganosiloxane is amodimethicone.

6. The method according to claim 1, wherein the granules are formed by contacting the solid particulate carrier with an emulsion comprising the non-elastomeric polyorganosiloxane under conditions such that the non-elastomeric polyorganosiloxane in liquid form is agglomerated with the solid particulate carrier.

7. The method according to claim 1, wherein the composition comprises at least 80 wt % of the solid particulate carrier and the non-elastomeric polyorganosiloxane.

8. The method according to claim 5, wherein the granules are formed by contacting the solid particulate carrier with an emulsion comprising the non-elastomeric polyorganosiloxane under conditions such that the non-elastomeric polyorganosiloxane in liquid form is agglomerated with the solid particulate carrier.

9. The method according to claim 5, wherein the composition comprises at least 80 wt % of the solid particulate carrier and the non-elastomeric polyorganosiloxane.

* * * * *